(12) United States Patent
Lebner

(10) Patent No.: US 7,511,185 B2
(45) Date of Patent: *Mar. 31, 2009

(54) BANDAGE FOR WOUND OR INCISION CLOSURE

(75) Inventor: Michael Lebner, Wellesley Hills, MA (US)

(73) Assignee: Clozex Medical LLC, Wellesley Hills, MA (US)

( * ) Notice: Subject to any disclaimer, the term of this patent is extended or adjusted under 35 U.S.C. 154(b) by 359 days.

This patent is subject to a terminal disclaimer.

(21) Appl. No.: 10/938,163

(22) Filed: Sep. 10, 2004

(65) Prior Publication Data

US 2005/0033215 A1    Feb. 10, 2005

Related U.S. Application Data

(60) Division of application No. 10/655,941, filed on Sep. 5, 2003, now Pat. No. 6,822,133, which is a continuation of application No. 10/014,832, filed on Dec. 11, 2001, now Pat. No. 6,831,205, which is a continuation-in-part of application No. 09/450,488, filed on Nov. 29, 1999, now Pat. No. 6,329,564.

(51) Int. Cl.
*A61F 13/00* (2006.01)
*A61B 17/08* (2006.01)

(52) U.S. Cl. .................. 602/41; 602/54; 606/213; 606/215

(58) Field of Classification Search ............ 602/41–59; 606/213–216
See application file for complete search history.

(56) References Cited

U.S. PATENT DOCUMENTS 363,538 A    5/1887   Penny 1,074,413 A    9/1913   De Baun et al.

(Continued)

FOREIGN PATENT DOCUMENTS

GB    1299367    12/1972

(Continued)

OTHER PUBLICATIONS

Packaging and instruction sheet for "umbillical hernia plaster" produced by Lohmann GmbH & Co., KG (Postflach 23 43, D-56513 Neuwied, Germany); undated.

(Continued)

*Primary Examiner*—Kim M Lewis
(74) *Attorney, Agent, or Firm*—Pierce Atwood LLP; Kevin M. Farrell; Katherine A. Wrobel

(57) ABSTRACT

Disclosed is a bandage for closing a wound or incision, and methods for the use of same. The bandage comprises a first flat flexible component having adhesive on a lower surface and one or more first elongated connectors extending in an offset manner from one edge thereof in a first direction. The bandage further comprises a second flat flexible component having adhesive on a lower surface and one or more second elongated connectors extending in an offset manner from one edge thereof in a second direction generally opposite to the first direction. Pulling elements are joined to the first and second elongated connectors. Means are provided for attaching the first elongated connectors to the second flat flexible component and the second elongated connectors to the first flat flexible component.

14 Claims, 6 Drawing Sheets

U.S. PATENT DOCUMENTS

| | | | |
|---|---|---|---|
| 1,230,444 A | 6/1917 | Teed |
| 1,969,188 A | 8/1934 | Spicer |
| 2,196,296 A | 4/1940 | Flynn |
| 2,532,011 A | 11/1950 | Dahlquist et al. |
| 2,762,371 A | 9/1956 | Guio |
| 2,818,865 A | 1/1958 | Jacoby, Jr. |
| RE24,906 E | 12/1960 | Ulrich |
| 3,020,186 A | 2/1962 | Lawrence |
| 3,329,548 A | 7/1967 | Blatz |
| 3,389,827 A | 6/1968 | Abere |
| 3,645,835 A | 2/1972 | Hodgson |
| 4,112,213 A | 9/1978 | Waldman |
| 4,141,363 A | 2/1979 | James et al. |
| 4,310,509 A | 1/1982 | Berglund et al. |
| 4,323,557 A | 4/1982 | Russo et al. |
| 4,328,057 A | 5/1982 | Gutow |
| 4,374,520 A | 2/1983 | Grossmann |
| 4,413,621 A | 11/1983 | McCracken |
| 4,423,731 A | 1/1984 | Roomi |
| 4,472,480 A | 9/1984 | Olson |
| 4,485,809 A | 12/1984 | Dellas |
| 4,499,896 A | 2/1985 | Heinecke |
| RE31,887 E | 5/1985 | Hodgson |
| 4,524,095 A | 6/1985 | Gockel et al. |
| 4,531,521 A | 7/1985 | Haverstock |
| 4,545,371 A | 10/1985 | Grossmann |
| 4,549,063 A | 10/1985 | Ang |
| 4,587,146 A | 5/1986 | Anhauser |
| 4,590,022 A | 5/1986 | Cioca |
| 4,595,001 A | 6/1986 | Potter |
| 4,595,011 A | 6/1986 | Phillips |
| 4,596,738 A | 6/1986 | Metcalfe |
| 4,600,001 A | 7/1986 | Gilman |
| 4,614,183 A | 9/1986 | McCracken |
| 4,646,731 A | 3/1987 | Brower |
| 4,664,106 A | 5/1987 | Snedeker |
| 4,678,462 A | 7/1987 | Vaillancourt |
| 4,706,662 A | 11/1987 | Thompson |
| 4,737,410 A | 4/1988 | Kantner |
| 4,753,232 A | 6/1988 | Ward |
| 4,787,380 A | 11/1988 | Scott |
| 4,825,866 A | 5/1989 | Pierce |
| 4,830,914 A | 5/1989 | Vaillancourt |
| 4,926,850 A | 5/1990 | Lott et al. |
| 4,950,282 A | 8/1990 | Beisang |
| RE33,353 E | 9/1990 | Heinecke |
| RE33,727 E | 10/1991 | Sims |
| 5,088,483 A | 2/1992 | Heinecke |
| 5,106,383 A | 4/1992 | Mulder |
| 5,135,518 A | 8/1992 | Vera |
| 5,160,315 A | 11/1992 | Heinecke |
| 5,176,703 A | 1/1993 | Peterson |
| 5,234,462 A | 8/1993 | Pavletic |
| 5,263,970 A | 11/1993 | Preller |
| 5,336,162 A | 8/1994 | Ota |
| 5,425,702 A | 6/1995 | Carn et al. |
| 5,531,855 A | 7/1996 | Heinecke et al. |
| 5,534,010 A | 7/1996 | Peterson |
| 5,685,833 A | 11/1997 | Turngren |
| 5,733,251 A | 3/1998 | Johns |
| 5,733,570 A | 3/1998 | Chen |
| 5,738,642 A | 4/1998 | Heinecke et al. |
| 5,779,659 A | 7/1998 | Allen |
| 5,849,325 A | 12/1998 | Heinecke |
| 5,891,078 A | 4/1999 | Turngren |
| 5,979,450 A | 11/1999 | Baker et al. |
| 5,981,823 A | 11/1999 | Turngren |
| 6,007,564 A | 12/1999 | Haverstock |
| 6,043,406 A | 3/2000 | Sessions et al. |
| 6,129,971 A | 10/2000 | Brandt |
| 6,149,614 A | 11/2000 | Dunshee |
| 6,155,999 A | 12/2000 | Bartlett |
| 6,169,224 B1 | 1/2001 | Heinecke |
| 6,264,976 B1 | 7/2001 | Heinecke |
| 6,329,564 B1 | 12/2001 | Lebner |
| 6,364,188 B1 | 4/2002 | Dunshee |
| 6,420,622 B1 | 7/2002 | Johnston |
| 6,436,432 B2 | 8/2002 | Heinecke |
| 6,461,467 B2 | 10/2002 | Blatchford |
| 6,495,230 B1 | 12/2002 | do Canto |
| 6,548,727 B1 | 4/2003 | Swenson |
| 6,566,575 B1 | 5/2003 | Stickels |
| 6,596,917 B2 | 7/2003 | Oyaski |
| 6,607,799 B1 | 8/2003 | Heinecke |
| 6,822,133 B2 | 11/2004 | Lebner |
| 6,831,205 B2 | 12/2004 | Lebner |
| 6,982,359 B1 | 1/2006 | Beaudry |
| 7,074,982 B2 | 7/2006 | Knutson et al. |
| 2004/0106888 A1 | 6/2004 | Lutri et al. |
| 2004/0204740 A1 | 10/2004 | Weiser |
| 2004/0243040 A1 | 12/2004 | Weiser |
| 2005/0182443 A1 | 8/2005 | John |

FOREIGN PATENT DOCUMENTS

WO    WO2005/079674 A1    1/2005

OTHER PUBLICATIONS

Stalar: "A more effective way to wound closure," by S. Paris, Abstract, Pub. by 43 Inter'l Sci. and Eng. Fair, Nashville, Tennessee, May 10, 1992, p. 257.

Paris, Stacy: "Is there a more effective way to accomplish wound closure than those presently employed?"; author indicates abstract published by South Carolina Junior Academy.

BANDAGE FOR WOUND OR INCISION CLOSURE

BACKGROUND OF THE INVENTION

Compositions and methods for wound or incision closure are known in the art. The use of sutures or staples to close a wound or incision represents the most common of these prior art techniques. The use of sutures or staples is an invasive technique which can be painful and frequently the use of an anesthetic is required. These processes often leave unsightly scars, both from the insertion holes and from varying tensions applied to the wound or surgical incision between the suturing points and intervening spaces. Moreover, these methods necessitate follow-up visits to a hospital or doctor's office for removal.

Although other compositions and methods for closing wounds or incisions are known in the art, these have not gained popular acceptance due to limitations in their design. There is a clear need for non-, or less invasive method for wound or incision closure which is practical and easy to use.

SUMMARY OF THE INVENTION

The present invention relates to a bandage for closing a wound or incision. The invention was originally disclosed in compliance with the U.S. Patent Office Disclosure Document Program as Disclosure Document Numbers 448,944 and 446,186. In a preferred embodiment, the bandage comprises a first flat flexible component having adhesive on a lower surface and a plurality of first elongated connectors extending from one edge thereof in a first direction. The bandage further comprises a second flat flexible component having adhesive on a lower surface and one or more second elongated connectors extending from one edge thereof in a second direction generally opposite to the first direction. A first pulling element is joined to the first elongated connectors and adapted for lateral translation of the first flat flexible component toward a wound edge. A second pulling element is joined to the second elongated connectors and adapted for lateral translation of the second flat flexible component toward the wound edge. The pulling elements tend to spread the pulling force provided by a person applying the bandage of the present invention across each of the elongated connectors to which it is attached. A means for attaching the first elongated connectors to the second flat flexible component and means for attaching the second elongated connectors to the first flat flexible component are provided.

The adhesives provided on the lower surface of the first and second flat flexible components are selected based on their compatibility with the skin, as well their ability to securely hold the bandage for a period of time sufficient for the wound to heal. A variety of such adhesives are known in the art. Prior to application, the adhesives are protected from contamination and oxidation by one or more sheets of a protective film. The film is removed prior to application of the bandage thereby exposing the adhesive.

In embodiments of the present invention in which the first and second flat flexible components are thin and extremely flexible, the adhesive protecting film may be selected to provide a degree of stiffness which aids in application of the bandage. Multiple protective films may be provided to protect the adhesive on a single flat flexible component, thereby providing convenient locations to grip the top and protected bottom of the bandage with the fingers during application.

The means for attaching the first elongated connectors to the second flat flexible component, and the second elongated connectors to the first flat flexible component, are also, in preferred embodiments, adhesives. When the flat flexible components are applied, and a desired tension is reached effecting wound or incision closure, the elongated connectors are brought into contact with the flat flexible components and an adhesive fixes their positions relative to one another. It will be recognized that during manufacture, the adhesive may be applied to the upper surfaces of the flat flexible components, to the lower surfaces of the elongated connectors, or to both. A variety of pressure sensitive adhesives are appropriate for this application and the choice of which adhesive to employ is largely one of design choice and optimization. As was discussed above in connection with the adhesive on the lower surfaces of the flat flexible components, the adhesives are protected prior to application with a thin removable film.

The sizes of the various components are variable within parameters defined by functional considerations. For example, the length of the first and second flat flexible components (i.e., in a dimension generally parallel to the wound or incision), must be approximately the same length as the wound or incision to effect closure. To a large extent, the length of the first and second flat flexible components (which is determined based on the length of the wound or incision) determines the width of the first and second flat flexible components (i.e., the dimension perpendicular to the length of the first and second flat flexible components in the plane of application). In other words, the relationship of length to width must be selected such that sufficient adhesive may be applied to hold the bandage in place once applied to the skin. If the width of the bandage is too small, relative to its length, the bandage will be insecure when applied and susceptible to premature and unintended separation from the skin. The determination of length to width ratios are empirical in nature and adhesive-dependent. Generally speaking, an acceptable length to width ratio may be from about 1:2 to about 8:1. These ratios are provided as examples, with no attempt being made to provide maximum or minimum ratios.

Another consideration which relates to the sizing of the elements of the bandage of the present invention is the spacing between the elongated connectors. It is important that there be sufficient space between adjacent elongated connectors to allow adjustment of the first and second flat flexible components relative to one another. More specifically, in application, one of the two flat flexible components is applied to the skin before the other flat flexible component. Following application, this flat flexible component is not easily removed and repositioned. Therefore, having sufficient spacing between the elongated connectors is important to facilitate fine adjustment of the unattached flat flexible component relative to the attached flat flexible component. There is no absolute minimum which can be stated with respect to spacing between elongated connectors. Preferred ranges are probably best stated as a percentage of the bandage length. For example, a spacing between adjacent elongated connectors of between about 5% to about 10% of the bandage length (as defined above) is an example of an appropriate range.

In preferred embodiments, the flat flexible components, elongated connectors, and pulling elements described in the preceding paragraph are produced from a substantially inelastic polymeric material. Alternatively, they may be produced from an elastic material which is reinforced with an inelastic structural component thereby rendering the device substantially inelastic. For example, such inelastic materials may include monofilament polymeric line or mesh. Reinforcement of the flat flexible components along the wound edge, and of the pulling elements, is preferably done using a material which is both rigid and inelastic (e.g., a rigid polymer is a preferred material for this purpose).

In preferred embodiments, the flat flexible elements, elongated connectors and pulling elements are produced from sheet stock (e.g., plastic sheet stock). Die cutting these elements from plastic sheet stock to provide monolithic components which are subsequently joined to produce a functional bandage is a particularly cost-effective approach. The sheet stock may be perforated to allow for the exchange of air with the skin beneath the bandage. The thickness of the sheet stock may vary depending upon application. In addition, as discussed above, portions may be reinforced with a rigid material as needed.

In preferred embodiments, the first and second pulling elements are removable following application of the bandage to the skin. This feature minimizes the bandage size following application to the patient. This decrease in the overall size of the bandage reduces the chance that a portion of the bandage may be caught, for example, on clothing or a pillow. Such an occurrence could tend to pull the bandage away from the skin thereby causing the wound or incision to open. Minimizing the overall size of the bandage following application also tends to provide for a more comfortable fit.

A preferred design which provides for the removal of the pulling elements includes in-line perforations or scoring along the first and second elongated connectors. By breaking the elongated connectors along these perforations, the first and second pulling elements are removed.

In a preferred embodiment of the bandage of the present invention, the first and second elongated connectors are interleaved. The interleaving of the elongated connectors can be effected in a variety of ways which will be apparent to one of skill in the art. By way of example, at least one member of the pair of flat flexible components and elongated connectors may be die cut as a single unit, while die cutting the corresponding pulling element separately. The first and second elongated connectors may then be interleaved, followed by attachment of the individually die cut pulling element to the appropriate elongated connectors using, for example, an adhesive.

Another method for assembling an interleaved embodiment is most readily described by way of example. A first monolithic component comprising a pulling element, a pair of first elongated connectors, and a first flat flexible component is provided. A second monolithic component comprising a pulling element, three second elongated connectors, and a second flat flexible component is provided. The elongated connectors are spaced such that they would interleave, if mated, but for the fact that the middle second elongated connector (being fixed at each end) prohibits the mating of the two elements. In order to mate the two monolithic components it is necessary to cut this middle second elongated connector, mate the two monolithic components such that the elongated connectors interleave, then reattach the middle second elongated connector. Clearly this method of assembling applies also to embodiments having more than 5 total elongated connectors.

An alternative to the interleaved embodiments described above has been termed the wide key-hole design. In this design, two monolithic components are manufactured (e.g., by a die cut process). Each of the two monolithic components comprise a first flat flexible component, elongated connector(s) and a pulling element. The elongated connector(s) of the first monolithic component are all adjacent to one another and centrally located in the assembled and applied bandage. The elongated connectors of the second monolithic component flank those of the first monolithic component lying toward the outside edges of the bandage. This design facilitates manufacture because both monolithic components can be die cut in a conventional manner, then the first monolithic component may be inserted into the relative wide opening between the two sets of elongated connectors in the second monolithic component. When rotated into the same plane, as they are when applied, the monolithic components engage one another resulting in a preferred embodiment of the present invention.

In another embodiment, the present invention relates to a wound closure device of the type described above, but having only a single elongated connector extending from the first flat flexible component, and a single elongated connector extending from the second flat flexible component. This embodiment is preferred for use in connection with relatively small wounds or incisions. Generally speaking, the width of the flat flexible components of this small wound embodiment is less than about ¾". This preference for use in connection with relatively small wounds or incisions is based on the fact that the elongated connector extends from its corresponding flat flexible component in an offset manner (i.e., not from the center of the wound edge, but rather to one side of the wound edge). If the flat flexible component were sufficiently wide, say two inches in width, attempts to effect adjustment of the wound edge could be distorted by flexing of the components. On the smaller scales anticipated in connection with this embodiment, the risk of this type of distortion is substantially eliminated.

By designing this embodiment so that the single elongated connector extends from its associated flat flexible component in an Offset manner, it is possible to apply each component of the two-component device such that the wound edge of each are substantially parallel and centrally aligned, with the elongated connectors of each component being substantially parallel. In use, the adhesive backed portion of the elongated connector extending from the first flat flexible component attaches to the second flat flexible component. Similarly, the adhesive backed portion of the elongated connector extending from the second flat flexible component attaches to the first flat flexible component. Care is taken during the design and manufacture process to ensure that adhesive is not applied to an elongated connection at a location which would result in contact between adhesive and the wound.

A pulling element is provided which extends from each elongated connector on the side of the elongated connector opposite the associated flat flexible component. In preferred embodiments, the pulling element is removable once the device is secured. A perforation in the material from which the device is constructed, along a line substantially perpendicular to the major axis of each elongated connector, is provided for easy removal of the pulling element. Optional features of the type described herein, in connection with other embodiments, are equally applicable to the single elongated connector embodiment.

When applied to the skin and appropriately tensioned, one edge of the first flat flexible component and one edge of the second flat flexible component are positioned nearest to and substantially parallel to the wound or incision. These edges will be referred to herein as the wound edges. In preferred embodiments of the present invention, the wound edges are adapted to evert (or raise) skin edges to promote wound healing. It is known in the art that everting, raising or mounding of the skin edges at the wound or incision site prevents wound inversion. One way in which this may be accomplished is to provide a bend at the wound edge. The bend may be angled or arcuate. The adhesive on the lower portion of the flat flexible components is also applied to the portion of the wound edge. When attached to the skin this eversion edge tends to lift the edges of the skin at the point of closure contact, thereby promoting wound or incision healing.

As mentioned above, preferred embodiments of the present invention include die cut embodiments. In such embodiment, the elongated connectors may be viewed as strap-like in their dimensions. In preferred embodiments, a portion of the elongated connectors is cut away to increase the unobstructed surface area over the wound or incision. This tends to facilitate drainage of exudates and application of medication. This cut-away is best made in a die cut process.

In preferred embodiments, the bandage of the present invention is also adapted for wound closure alignment. Spacing between adjacent elongated connectors, as discussed above, is relevant to the issue of wound closure alignment. Additionally, preferred embodiments of the bandage of the present invention include wound closure alignment indicators. These alignment indicators are visual indicators which appear on the flat flexible components near the wound edge. Typically, they will appear as a line or an arrow generally perpendicular to the wound or incision. In closing a wound or incision, a clinician typically closes the wound manually with his/her fingers at the approximate mid-point, then makes a small mark or line perpendicular to the wound with a surgical pencil. These marks are used to align the device precisely with the wound alignment indicators on the bandage of the present invention.

The bandage of the present invention can be optionally adapted for transdermal drug delivery. As is known in the art, a drug is deliverable transdermally through the skin. For such an application, a drug-containing patch is secured to at least one of the flat flexible components in such a way that the drug can be delivered through the skin. Given the fact that there will be no adhesive contact between the skin and the flat flexible component in the area of the drug delivery patch, it may be necessary to increase the size of the flat flexible component to secure the bandage in such a transdermal drug delivery embodiment. Transdermal drug delivery is well known in the art and a review of the background is not necessary to enable one of skill in the art to make and use the present invention.

The bandage of the present invention may optionally include an elastic tension indicator element. The purpose of the tension indicator element is to provide a visual indication that a desired tension has been reached while applying the bandage. For example, materials are known in the art which change color when a predetermined tension is applied. Similarly, other graphic representations may be used for this purpose. For example, a rectangular graphic representation may be applied to an elastic tension indicator element. As this tension indicator is stretched, the graphic representation of the rectangle stretches. This element may be designed such that the desired tension is indicated when the original rectangular representation is stretched to the point where it closely approximates a geometric square.

It is desirable that this elastic tension indicator element be removable with the pulling elements following application of the bandage. At a minimum, the elastic tension indicator element should be positioned in the bandage such that when the bandage is applied, it is not possible for the elastic element to continue to stretch and release the desired tension previously established.

The present invention also relates to a method of wound closure. The method comprises applying the bandage described above in the manner specified.

The device of the present invention can also be adapted for skin stretching prior to a surgical procedure. Consider, for example, a situation in which a surgeon wishes to remove an abnormal skin patch. If the skin patch is generally round, having a diameter of one inch, it is easy to imagine the problem associated with closing the incision resulting from its removal. Currently this problem is addressed by stretching the skin using an invasive procedure in which a balloon-like device is inserted beneath the skin, and inflated. Over a period of days, the skin above the device is stretched and the removal of the undesirable skin patch creates an opening in the skin which is much more easily closed.

The device of the present invention can be used to accomplish this skin-stretching function. This is accomplished by placing the wound edges of each component of the two-component device on either side of the skin patch to be excised. The device is then tensioned as described herein. In light of the fact that the distance between the two wound edges is relatively large in this application, the tension on the device is increased. To ensure adherence of the components of the device in this skin-stretching embodiment, it is desirable to provide adhesive on the pulling elements of the device. In this embodiment, not only are the components secured by adhesive contact between the elongated connector(s) and flat flexible components, but also by adhesive contact between pulling elements and the skin. In this embodiment the pulling elements are not removed following application of the device.

DETAILED DESCRIPTION OF PREFERRED EMBODIMENTS

Figure 1:
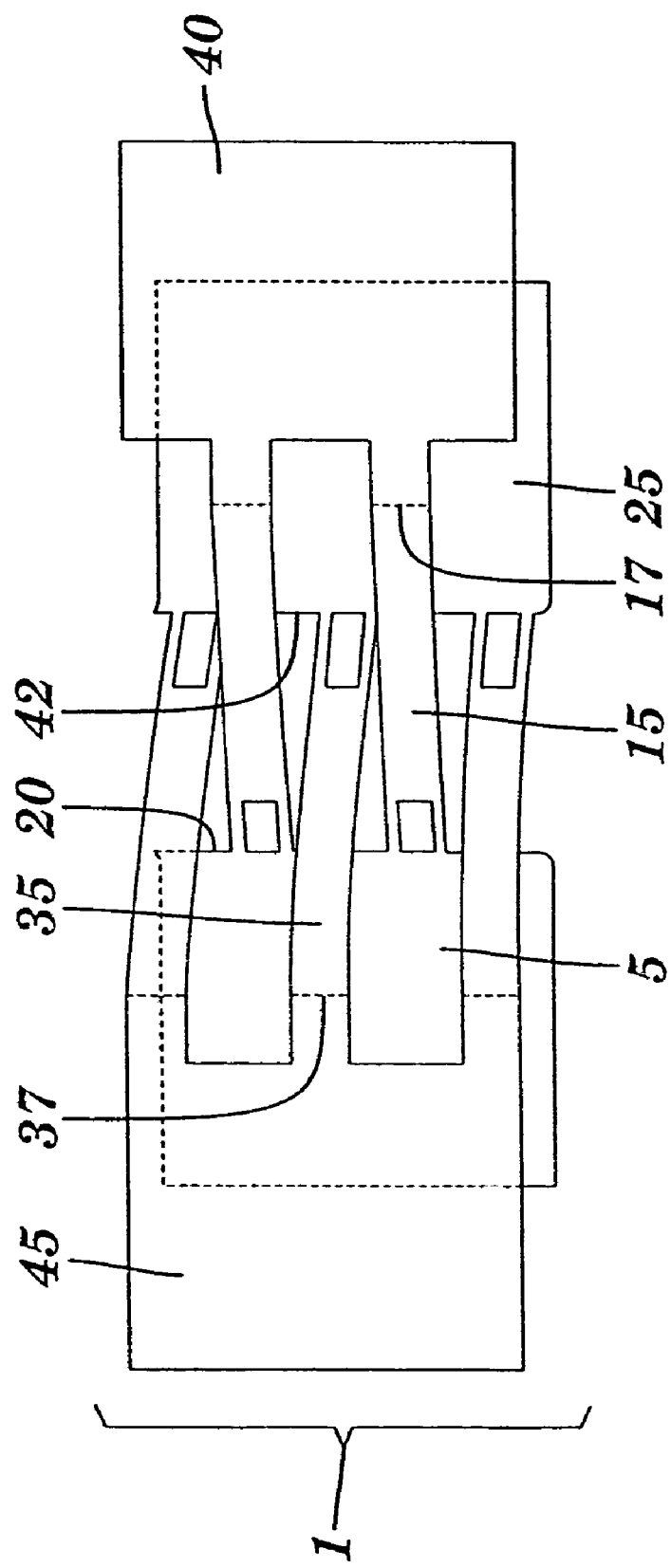
FIG. 1 is a perspective view illustrating a bandage of the present invention in a non-tensioned state.

A bandage of the present invention in a non-tensioned state is depicted in FIG. 1. Bandage (1) includes a first flat flexible component (5) and a second flat flexible component (25). Each of these components has an upper surface to which lead lines 5 and 25 are directed, and lower surfaces which are not visible in the drawing. The lower surfaces are coated with adhesive to facilitate attachment to the skin. A plurality of first elongated connectors (15) extend from the wound edge (20) of the first flat flexible component (5) in a first direction, and a plurality of second elongated connectors (35) extend from the wound edge (42) of the second flat flexible component in a second direction which is generally opposite to the first direction. A first pulling element (40) is joined to the first elongated connectors (15) and adapted for lateral translation of the first flat flexible component (5) toward a wound or incision. Similarly, a second pulling element (45) is joined to the second elongated connectors (35) and adapted for lateral translation of the second flat flexible component (25) toward the wound or incision. In preferred embodiments, the means for attaching the first elongated connectors (15) to the second flat flexible component (25), and the second elongated connectors (35) to the first flat flexible component (5), comprise an adhesive. The adhesive may be applied to the lower surfaces of the first and second elongated connectors (15 and 35), or to the upper surfaces of the first and second flat flexible components (5 and 25). Perforations (17 and 37) in the elongated connectors facilitate removal of the pulling elements (40 and 45) from the elongated connectors (15 and 35) following application of the bandage.

Lower surfaces of the first and second flat flexible components are covered (at least partially) with adhesive to facilitate attachment to the patient's skin. Such adhesives facilitate attachment and allow easy removal of the bandage after the wound or incision has healed. Protective films (not shown), removable by hand, serve as means for protecting the adhesive on the first and second flexible flat components (5 and 35) prior to use of the bandage.

Figure 2:
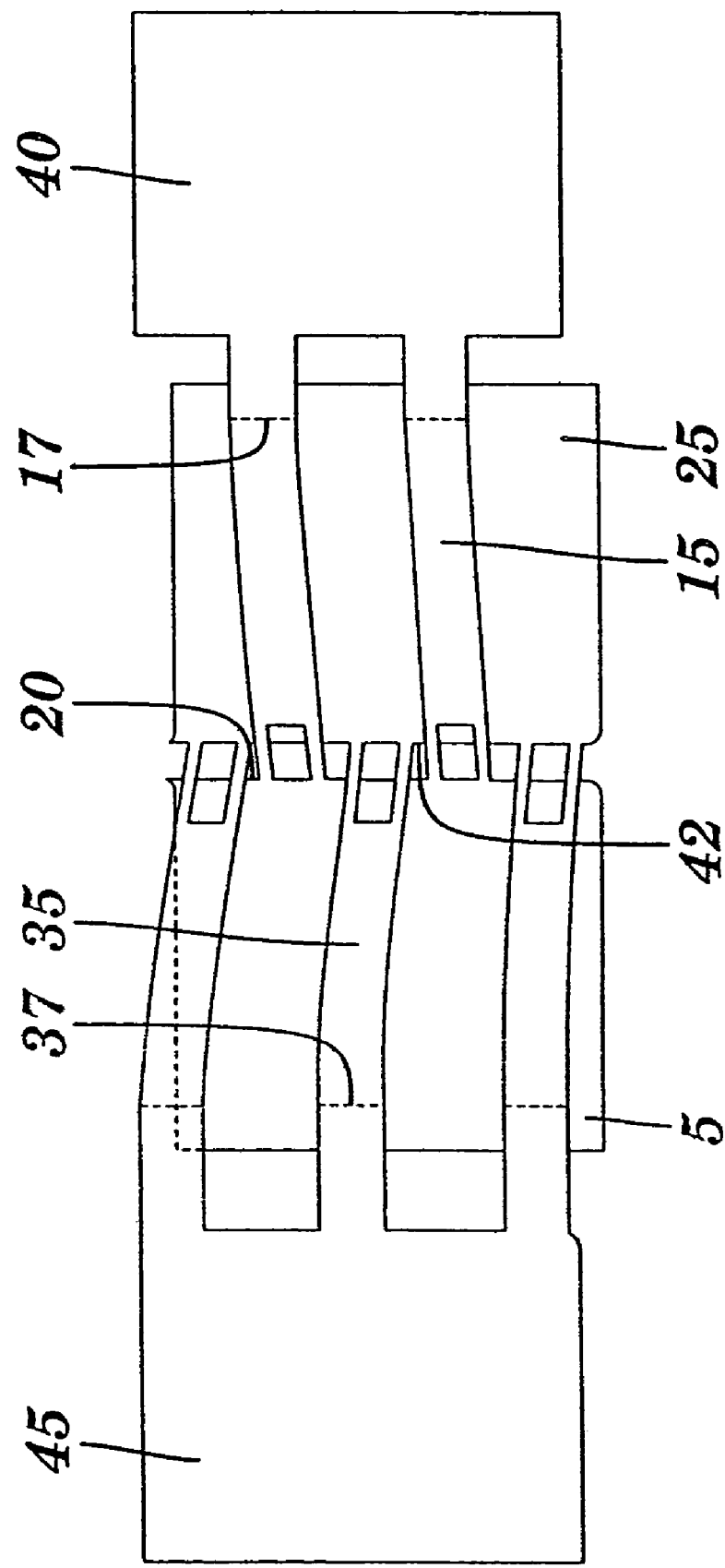
FIG. 2 is a perspective view illustrating a bandage of the present invention with tension applied.

FIG. 2 depicts the bandage of FIG. 1 in a tensioned, but non-fixed state. More specifically, FIG. 2 depicts first and second flat flexible components (5 and 25) attached to the skin with adhesive. Tension has been applied to pulling elements (40 and 45) thereby drawing wound edges (20 and 42) toward one another, thereby effecting wound closure. Elongated connectors (15 and 35) have not yet been fixed by adhesive to the flat flexible components (5 and 25), thereby completing application.

Figure 3:
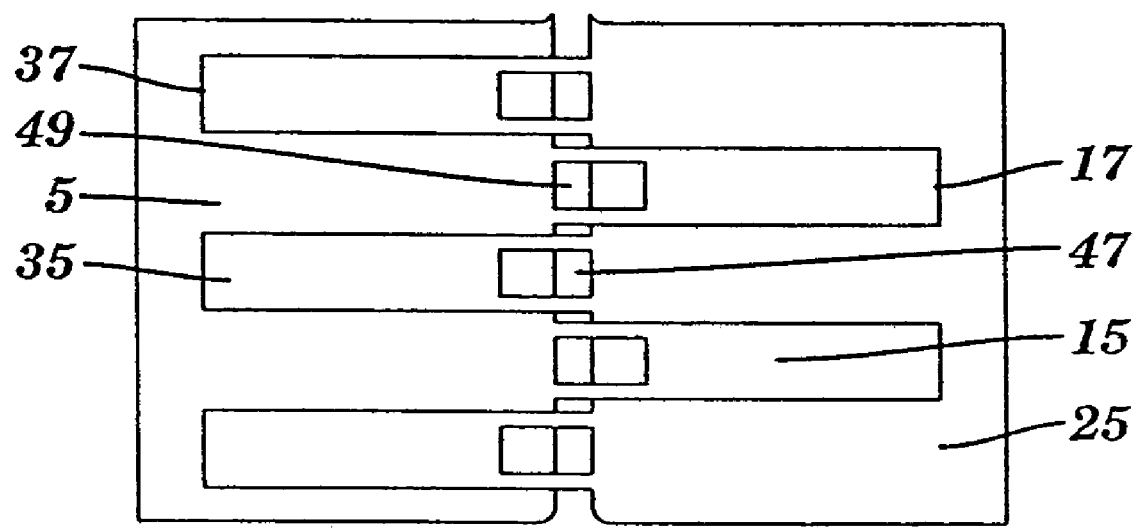
FIG. 3 is a perspective view illustrating a bandage of the present invention with elongated connectors secured to flat flexible components and pulling elements removed.

FIG. 3 depicts the bandage of FIG. 1 in the tension and fixed (i.e., applied) state. Pulling elements 40 and 45 as shown in FIGS. 1 and 3 have been removed along perforations 17 and 37. Elongated connectors 15 and 35 are attached to flat flexible components 5 and 25 by adhesive. Cut-outs (47 and 49) in elongated connectors (35 and 15) are positioned directly above the wound or incision to facilitate drainage of exudates and application of medication.

Figure 4:
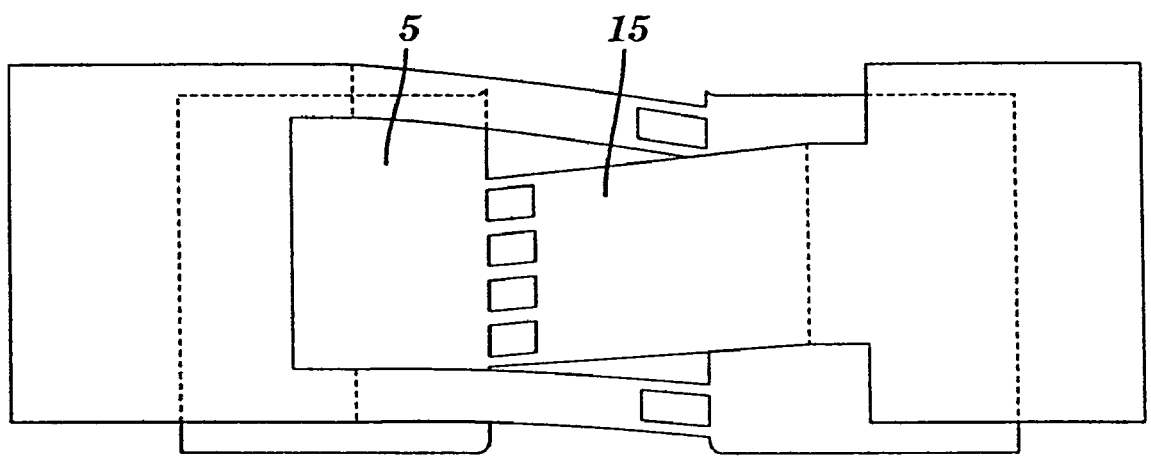
FIG. 4 is a perspective view illustrating a bandage of the present invention in non-tensioned a wide-keyhole embodiment.

Referring to FIG. 4, an alternative embodiment of the bandage of FIG. 1 is shown in which only a single elongated connector (15) is attached to the first flat flexible component (5). This embodiment is referred to herein as a wide key-hole embodiment.

Figure 5:
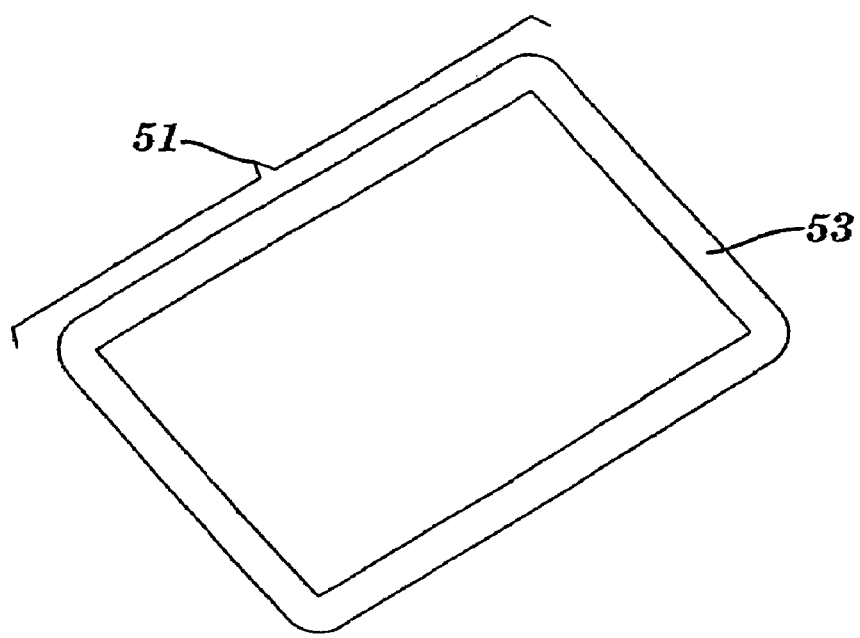
FIG. 5 is a perspective view of a protective cover for application over the bandage of the present invention.
Figure 6:
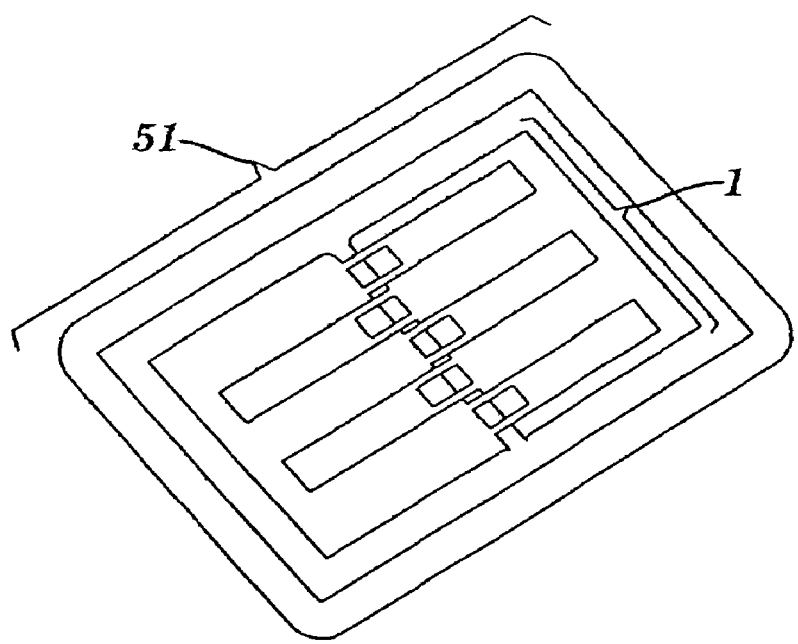
FIG. 6 is a perspective view of the protective cover of FIG. 6, applied to protect a bandage of the present invention.

Referring to FIG. 5, a clear, breathable protective cover (51) having an adhesive strip (53) along the perimeter may be applied to protect the area to which a bandage of the present invention has been applied. FIG. 6 depicts the protective cover (51) applied to the skin over a bandage of the present invention (1).

Figure 7:
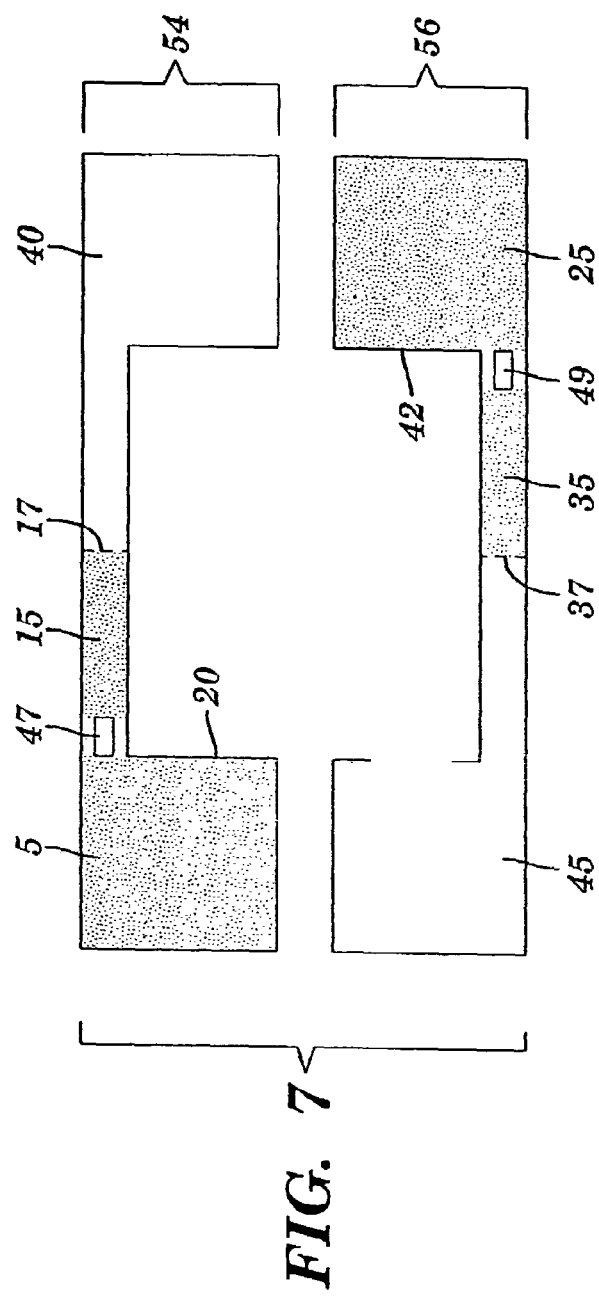
FIG. 7 is a perspective view illustrating an embodiment of the present invention in which each component of the two-component device comprises only a single elongated connector.

FIG. 7 is a diagrammatic representation of a two-component wound closure device of the present invention. The first component of the two-component device is indicated by reference number 54, and the second component of the two-component device is indicated by reference number 56. Each of the two components (54 and 56) have a single elongated connector (15 and 35) associated with each flat flexible component (5 and 25). The single elongated connectors (15 and 35) extend from their associated flat flexible components (5 and 25) in an offset manner. An example of an adhesive application pattern, intended to be non-limiting, for securing the two components is shown by shading. In preferred embodiments, the adhesive is applied to each flat flexible component (5 and 25), as well as a portion of the elongated connectors (15 and 35). Pulling elements (40 and 45) are provided for ease of application and adjustment of the two-components of the wound closure device. Perforations (17 and 37) are provided in preferred embodiments for removal of the pulling elements. In FIG. 7, the position of the perforation is near the central region of the elongated connectors. It will be recognized that the positioning of the perforations (17 and 37) is a matter of design choice. Cut-outs (47 and 49) are also shown in FIG. 7. These cut-outs are intended to allow for drainage of wound exudates, as well as to facilitate application of medication to the wound area.

Figure 8:
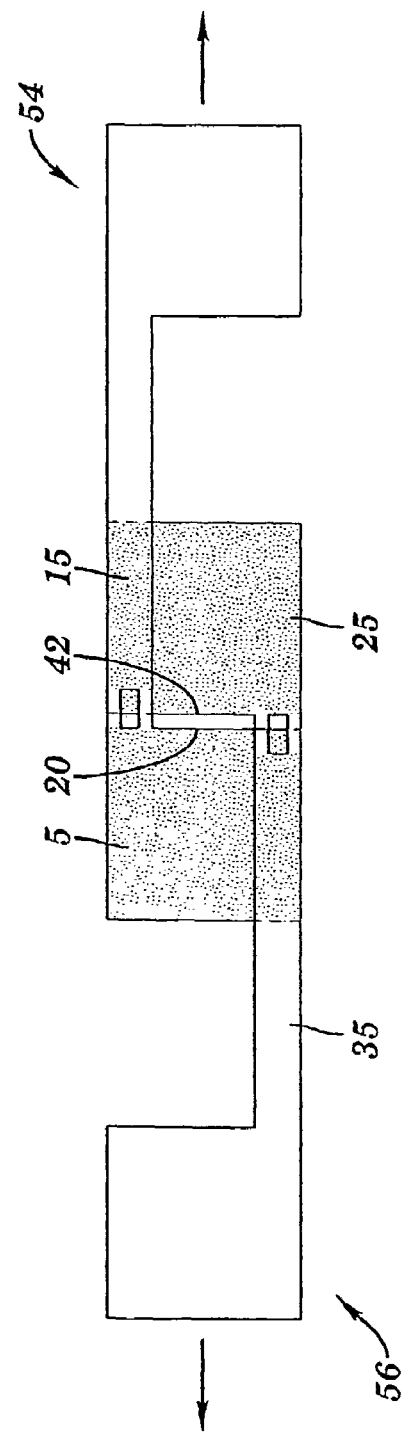
FIG. 8 is a perspective view depicting the device of FIG. 7 in use.

Referring to FIG. 8, in use, the offset enables the device to be positioned such that each component (54 and 56) of the two component device is aligned such that the wound edge of each (20 and 42) (i.e., the edge of the flat flexible component positioned nearest the wound or incision) are substantially parallel and centrally aligned, with elongated connectors (15 and 35) substantially parallel. While FIG. 8 depicts the offset of each elongated connector in its most extreme embodiment (i.e., one edge of each elongated connector extends linearly from one edge of each flat flexible component), it is not necessary that the elongated connectors be so severely offset. The degree of offset is sufficient when each component of the device can be positioned as taught herein without the first and second elongated connectors making contact with each other. When positioned, the adhesive backed portion of the elongated connector (15) extending from the first flat flexible component (5) attaches to the second flat flexible component (25). Similarly, the adhesive backed portion of the elongated connector (35) extending from the second flat flexible component (25) attaches to the first flat flexible component (5).

The invention claimed is:

1. A two-component medical device comprising:
   a) a first component comprising a first flat flexible component and a plurality of first elongated connectors extending from one edge thereof in a first direction;
   b) a second component comprising a second flat flexible component having one or more second elongated connectors extending from one edge thereof in a second direction generally opposite to the first direction wherein the plurality of first elongated connectors and the one or more second elongated connectors are interleaved;
   c) a first pulling element joined to said plurality of first elongated connectors and adapted for lateral translation of the first flat flexible component toward a wound edge, the first pulling element having adhesive on a lower surface and wherein the first pulling element is rigid;
   d) a second pulling element joined to said one or more second elongated connectors and adapted for lateral translation of the second flat flexible component toward the wound edge, the second pulling element having adhesive on a lower surface and wherein the second pulling element is rigid; and
   e) means for attaching the plurality of first elongated connectors to the second flat flexible component and means for attaching the one or more second elongated connectors to the first flat flexible component such that the plurality of first elongated connectors and the one or more second elongated connectors are sufficiently spaced apart to facilitate fine adjustment of the first flat flexible component relative to the second flat flexible component for substantially parallel alignment of the edge of the first flat flexible component with the edge of the second flat flexible component during closure of the wound or incision.

2. The medical device of claim 1 wherein elements a)-d) are produced from a substantially inelastic material or are produced from an elastic material which is reinforced with an inelastic structural component thereby rendering the device substantially inelastic.

3. The medical device of claim 1 wherein the first and second pulling elements are capable of being removed following attachment of the bandage.

4. The medical device of claim 1 wherein the first elongated connectors are adjacent to one another and centrally located, and the second elongated connectors flank the first elongated connectors at outside edges of the bandage.

5. The medical device of claim 1 wherein the first and second pulling elements are non-rigid, but are reinforced with a rigid element.

6. The medical device of claim 1 wherein the edges of the first and second flat flexible components which attach to the skin on opposing sides of a wound or incision are capable of everting skin edges to promote wound healing.

7. The medical device of claim 1 wherein the edges of the first and second flat flexible components are angled or curved to evert the skin edges.

8. The medical device of claim 1 wherein a portion of the elongated connector is cut away to increase unobstructed surface area above the wound thereby facilitating drainage of exudates and application of medication.

9. The medical device of claim 1 wherein the first and second flat flexible components are adapted for wound closure alignment.

10. The medical device of claim 9 wherein said adaptation comprises alignment marks on the first and second flat flexible components for alignment with each other and/or with marks placed directly on skin.

11. The medical device of claim 1 which is capable of transdermal drug delivery.

12. The medical device of claim 1 further comprising an elastic tension indication element.

13. The medical device of claim 12 wherein the elastic tension indication element is removable with the pulling elements.

14. The medical device of claim 1 further comprising a rigid polymer bar attached to the edges of the first and second flat flexible components which are nearest to and substantially parallel the wound or incision.

* * * * *